United States Patent [19]

Schlossman et al.

[11] Patent Number: 4,661,446

[45] Date of Patent: Apr. 28, 1987

[54] MONOCLONAL ANTIBODIES AND METHOD OF IMMUNIZING THEREWITH

[75] Inventors: Stuart Schlossman, Newton Center; Chikao Morimoto, Needham; Norman Letvin, Newton, all of Mass.

[73] Assignee: Dana-Farber Cancer Institute, Inc., Boston, Mass.

[21] Appl. No.: 703,219

[22] Filed: Feb. 19, 1985

[51] Int. Cl.$^4$ .............. C07K 15/04; C12N 5/00; G01N 33/577; G01N 33/569

[52] U.S. Cl. .................................. 435/7; 435/29; 435/68; 435/172.2; 435/240; 436/546; 436/548; 935/92; 935/104; 935/110; 530/387

[58] Field of Search ............. 260/112 R; 435/68, 240, 435/7, 29, 172.2, 188; 935/92, 95, 99, 100, 102-104, 106, 108, 110; 436/503, 518, 519, 520, 546, 547, 548, 815, 819, 824; 424/85; 530/387

[56] References Cited

U.S. PATENT DOCUMENTS 4,361,549  11/1982  Kung et al. .............................. 435/7
4,361,550  11/1982  Kung et al. .............................. 435/7

OTHER PUBLICATIONS

Tax, W. J. M. et al., Clin. Exper. Immunol. 55(2):427–436 (1984).
Schlossman, S. F. et al., *Progress in Immunology*, V. Academic Press Japan, Tokyo, Japan (1984), Yamamura, Y. et al., eds., pp. 1069–1078.
Ellingsworth, L. R. et al., Veterinary Immunology and Immunopathology, 2:54–553 (1981).
Haynes, B. F. et al., Science 215:298–299 (1982).
Clark, E. A. et al., Immunogenetics 18:599–615 (1983).
Letvin, N. L. et al., European J. of Immunology, 13:345–347 (1983).
Palley, L. S. et al., J. Med. Primatol. 13:67–71 (1984).
Balner, H. et al., Eur. Surg. Res. 14(6):447–448 (1982).
Dowell, B. L. et al., Human Immunol. 7(2):95–104 (1983).
Foon, K. A. et al., J. Immunogenetics, 11(3–4):233–244 (1984).
Martin, P. J. et al., J. Immunology, 131:180–185 (1983).
Martin, P. J. et al., J. Immunology, 132:759–765 (1984).

*Primary Examiner*—Charles F. Warren
*Assistant Examiner*—M. Moskowitz

[57] ABSTRACT

A method of distinguishing subsets within a plurality of human cells including producing a monoclonal antibody to a non-human primate cell, contacting the monoclonal antibody with the human cells, and distinguishing the subsets on the basis of different degrees of reactivity with the monoclonal antibody.

6 Claims, 8 Drawing Figures

UNSEPARATED T CELLS

T4 CELLS

T8 CELLS

MONOCLONAL ANTIBODIES AND METHOD OF IMMUNIZING THEREWITH

This invention was made with Government support and the Government has certain rights in the invention.

This invention relates to monoclonal antibodies.

Recent developments in hybridoma technology have demonstrated that human T cells can be divided into more than one functionally distinct subpopulation. For example, Reinherz et a., *Cell*, 19:821 (1980) and Reinherz et al., *Immunology Today*, 4:69 (1981) describe studies which indicate that certain T cell subsets have inducer functions, whereas other subsets have suppressor functions. Other studies have demonstrated that communicative interactions occur between and within the major T cell subsets in the generation of specific effector functions; Evans et al., *J. Immunol.*, 120:1423 (1978); Morimoto et al., *J. Immunol.*, 128:1645 (1982); Thomas et al., *J. Immunol.*, 125:2402 (1980); Gatenby et al., *J. Exp. Med.*, 156:55 (1982); and Yachi et al., *J. Immunol.*, 129:103 (1982). Because regulatory mechanisms are essential to the maintenance of immune homeostasis, an understanding of the interactions between the subsets is of considerable importance.

It has been shown that within the major T cell sets, T4 and T8, there exist both functional and phenotypic heterogeneity; Thomas et al., *J. Immunol.*, 125: 2402 (1980); Morimoto et al., *J. Immunol.*, 128: 1645 (1982); Gatenby et al., *J. Exp. Med.*, 156: 55 (1982); and Reinherz et al., *J. Immunol.*, 126: 67 (1981). Interaction between subpopulations of T4 and T8 cells, for example, is required to induce suppression of IgG production in antigen, pokeweed mitogen, or autologous leukocyte reaction-driven systems. Similarly, differentiation of T8 cytotoxic effectors from precytotoxic T8 lymphocytes in mixed leukocyte reactions has been shown to require the presence of T4 cells.

A number of monoclonal and autoantibodies have been developed which have provided an initial phenotypic definition of the heterogeneity within the major populations of these cells. Morimoto et al., *J. Clin. Invest.*, 67: 753 (1981) describes using naturally occurring anti-T cell antibodies found in some patients with active juvenile rheumatoid arthritis (JRA) to subdivide T4 cells into helper population (T4JRA−) and an inducer of suppressor subpopulation (T4JRA+) for pokeweed mitogen and antigen driven immunoglobulin production. Similarly, Reinherz et al., *J. Immunol.*, 128: 463 (1982) describes using antibody to Ia to divide T4 cells into T4Ia+ and T4Ia− subsets; both subsets were required to induce optimal Ig secretion by B cells.

SUMMARY OF THE INVENTION

In general, the invention features a monoclonal antibody and a method of distinguishing subsets within a plurality of human cells, preferably T cells such as T4 cells, which method includes producing a monoclonal antibody to a non-human primate cell such as a marmoset or chimpanzee T cell, contacting the monoclonal antibody with the human cells, and distinguishing the subsets on the basis of different degrees of reactivity with the monoclonal antibody.

The antibody is useful in the diagnosis and/or treatment of a disease, e.g., Juvenile Rheumatoid Arthritis (JRA), Sjogren's disease, or Systemic Lupus Erythematosis (SLE), caused or exacerbated by the immunizing subset. Diagnosis could be accomplished using flow cytometry to measure reactivity of cells, with the antibody conjugated with a fluorescent dye. To treat the disease, the antibody could be chemically coupled to a cytotoxic agent and administered to a patient suffering from the disease. The antibody would specifically bind to and destroy the disease-causing cells, but not the normal cells.

The method of the invention permits the division of an otherwise apparently homogeneous population (or "set") of human cells into unique subpopulations (or "subsets"), thus making possible diagnosis of such autoimmune diseases as Juvenile Rheumatoid Arthritis (JRA), Sjogren's disease, and Systemic Lupus Erythematosis (SLE), in which T cells are implicated.

Immunization of a mammal with a non-human primate cell thus can produce a monoclonal antibody which reacts to a greater degree with a first subset of a set of human cells than with a second subset, even though the two subsets exhibit substantially the same degree of reactivity with a different monoclonal antibody which defines the set; e.g., an antibody highly reactive with T4 cells but exhibiting little reactivity with T8 cells. Preferably the human cells are lymphocytes, e.g., B cells or T cells such as T4 or T8 cells.

It has been discovered that an additional benefit is realized by immunization of a mammal with non-human primate cells: for reasons which are as yet unclear, antigenic determinants common to a human and a non-human primate cells sometimes can exhibit greater immunogenicity in rodents, e.g., mice, when presented on the non-human cell, compared to the human cell. This may be because of a comparatively greater immunodominance of some determinants on non-human primate cells, perhaps owing to the expression of the determinant on the non-human cell in a more highly antigenic configuration. This discovery makes possible increased production of monoclonal antibodies against important but weakly antigenic determinants on human cells, by immunizing with a non-human primate cell also bearing the determinant.

The method of using non-human primate cells to produce a monoclonal antibody capable of dividing a set of human cells into subsets can be carried out with an additional step, to produce a monoclonal antibody which is specific for one of the subsets, as follows. Once a non-human primate-derived monoclonal antibody has been used to identify two distinct subsets of, say, human T4 cells (one subset being more reactive and the other less reactive with the antibody), one of the identified subsets (say the more reactive subset) can be used to immunize mice and to produce a plurality of hybridomas; the monoclonal antibodies produced by these hybridomas can then be screened against the immunizing subset and the other subset. An antibody more reactive with the immunizing subset than with the other subset defines the polymorphic surface structure or structures which differentiate the two subsets.

Other features and advantages of the invention will be apparent from the following description of the preferred embodiments thereof, and from the claims.

DESCRIPTION OF THE PREFERRED EMBODIMENTS

The drawings will first be described.

DRAWINGS

IMMUNIZATION WITH NON-HUMAN PRIMATE CELLS

Figure 1:
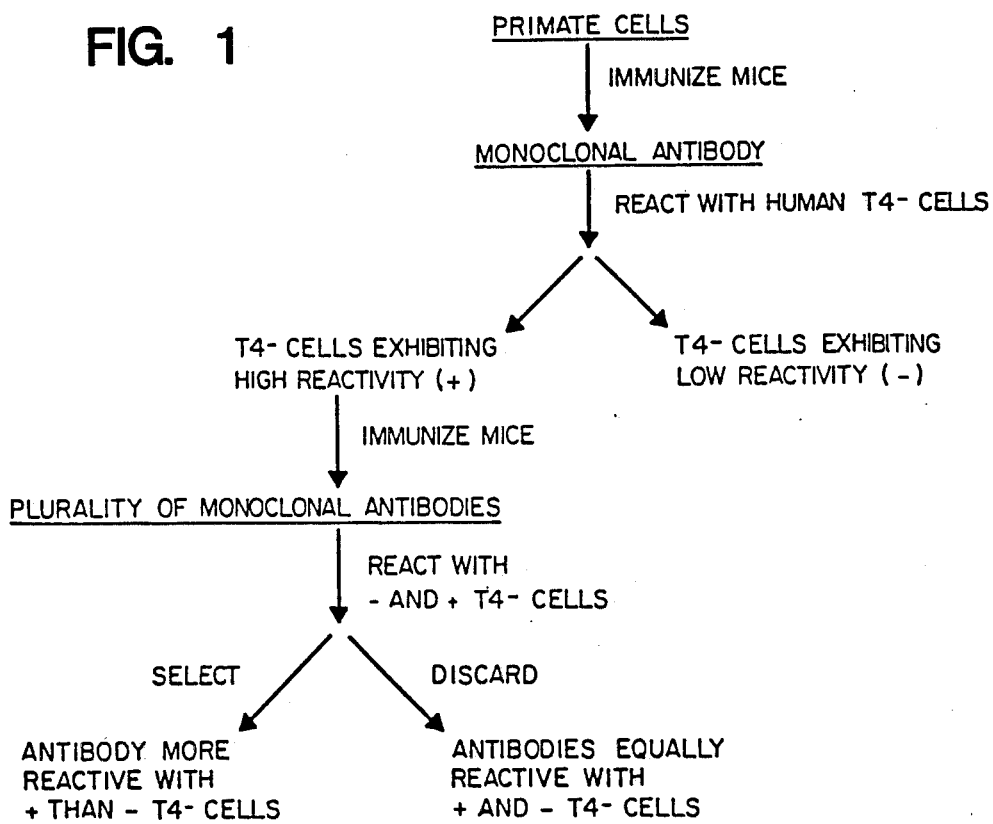
FIG. 1 is a flow chart of an antibody production method, discussed above.

The first step in the method is to select the non-human primate whose cells are to be used for immunization. The choice of primate depends in part on how phylogenetically distant the primate is from humans. This phylogenetic distance is generally reflected in the reactivity of a primate's cells with monoclonal antibodies of human origin.

Table 1, below, shows the reactivities of T-cells of various species with monoclonal antibodies produced by immunizing Balb/C or CAF1 mice with a variety of human T-cell subsets. Cells of chimpanzees, phylogenetically close to humans, react with all of the human cell-derived antibodies, while cells of the distant lemur react with none. Common marmoset T-cells are reactive with T4A and T8A, but with none of the other antibodies.

lines, T4 antigen specific inducer T cell lines, T4 antigen specific inducer of suppressor T cell lines, T8 suppressor lines, and freshly isolated activated T cells. Antibodies which are reactive with a fraction of the inducer or suppressor population but may or may not be unreactive with human B lines B-lymphocytes, mycloid cells and mycloid lines are isolated.

Such antibodies can then be used to divide a T4 or T8 population into subsets, based on the degree to which cells from each subset react with the antibodies. Such different reactivities will indicate either the existence of polymorphic epitopes in the structure of a single surface antigen which defines, say, T4 or T8; or the existence of a family of such surface antigens which define the T4 and T8 population, which family of antigens exhibits heterogeneity. In either case, the polymorphism or heterogeneity can be detected using primate-derived monoclonal antibodies. Given the variety of abnormalities in immunoregulatory subsets that exist in a number of autoimmune diseases, the definition of either polymorphic determinants or unique subsets can prove to be very important, given the fact that variations in structures of the MHC complex are of importance in predicting disease susceptibility.

Antibodies that react with subfractions of T4 and T8 populations of cells are characterized by indirect immunofluorescence, as follows. Approximately $10^6$ cells are incubated with either hybridoma supernatants or asci-

TABLE 1

| Species | SUPPRESSOR/CYTOTOXIC T CELL DETERMINANTS | | | | | HELPER/INDUCER T CELL DETERMINANTS | | | |
|---|---|---|---|---|---|---|---|---|---|
| | T8 | T5 | T8A | T8B | T8C | T4 | T4A | T4B | T4C |
| Man | $25 \pm 4^a$ | $20 \pm 1$ | $25 \pm 4$ | $25 \pm 4$ | $25 \pm 4$ | $41 \pm 2$ | $41 \pm 2$ | $41 \pm 2$ | $41 \pm 2$ |
| Chimpanzee | 51 | $39 \pm 1$ | $46 \pm 6$ | $54 \pm 4$ | $56 \pm 5$ | 27 | 35 | 32 | $31 \pm 4$ |
| Gibbon | $54 \pm 11$ | $40 \pm 5$ | $55 \pm 10$ | $51 \pm 8$ | $51 \pm 10$ | $25 \pm 1$ | $21 \pm 4$ | $19 \pm 4$ | <2 |
| Formosan rock macaque | $23 \pm 8$ | $20 \pm 4$ | <5 | $27 \pm 8$ | $28 \pm 7$ | $28 \pm 10$ | $27 \pm 10$ | <2 | $11 \pm 6$ |
| Owl Monkey | <5 | $26 \pm 3$ | <5 | <5 | $7 \pm 2$ | <2 | $45 \pm 0$ | $43 \pm 1$ | <2 |
| Common Marmoset | <5 | <5 | $21 \pm 2$ | <5 | <5 | <2 | $42 \pm 4$ | <2 | 7 |
| Galago | <5 | <5 | <5 | <5 | <5 | <2 | <2 | <2 | <2 |
| Lemur | N.T. | N.T. | N.T. | N.T. | N.T. | <2 | <2 | <2 | <2 |

*The data are expressed as the percent PBM staining positive ± S.D.

Non-human primate T cells can be used for immunization as follows. First, the cells are isolated from heparinized blood utilizing Ficoll-Hypague and density gradient centrifugation. The cells are then treated with 0.15M NH$_4$Cl to lyse erythrocytes, washed, resuspended in phosphate buffered saline, and used for immunization and frozen for subsequent screening.

Balb/C or CAF1 mice are then immunized with these cells using standard procedures. The splenocytes obtained are fused in PEG with P3/NS1/1-AG4-1 myeloma cells. Hybridoma culture supernatants reactive with immunizing cells, but partially reactive with human T cells or T cell lines, are then selected, and these lines are cloned and recloned by limiting dilution in the presence of feeder cells using standard techniques.

The initial screen is meant to identify antibodies reactive with primate T-cells and reactive with some but not all human T lymphocytes. Subsequent screening then involves the characterization of such antibodies on large panels of human T lymphocytes, including freshly isolated T4 cells, T4JRA-TQ1+, T4JRA-TQ1−, T4JRA+, T8 cells, T4 cytotoxic lines, T8 cytotoxic tes, washed at 4° C. extensively, and then stained with FITC anti-mouse IgG. The fluorescent antibody-coated cells are then analyzed on a FACs I, an EPICS V, or a similar instrument, which allow for a precise quantitative assessment of the number of reactive cells.

ANTI-4B4

A particular anti-primate cell monoclonal antibody, designated anti-4B4, was produced using standard techniques, as follows.

BALB/c J mice (Jackson Laboratories, Bar Harbor, ME) were immunized with cells of a T lymphocyte line derived from the cotton top tamarin *Saguinus Oedipus,* an herbivorous New World primate species. Peripheral blood lymphocytes from this species were stimulated in vitro with PHA and then maintained in continuous culture with T cell growth factors. Hybridoma cultures containing antibodies reactive with human (E+) cells were selected, cloned, and recloned by limiting dilution methods in the presence of feeder cells; E+ cells are known to be capable of defining T cell specific antibodies from those unreactive with T cells. Malignant ascites were then developed and utilized for analysis. The monoclonal antibody anti-4B4 was shown to be of the IgG1 isotype by specificity of staining with fluorescein-labeled goat anti-mouse IgG (Meloy Laboratories, Springfield, VA), and by it failure to be stained by fluorescein-labeled antibodies directed against other subclasses of mouse immunoglobulin.

PREPARATION OF T4+ and T8+ CELL SETS

Human E+ lymphocytes were treated with anti-T4 or anti-T8 monoclonal antibodies and rabbit complement (C) (Pel-Freeze Biologicals). $2 \times 10^7$ cell aliquots were incubated with 1 ml of antibody at a 1:250 dilution for 1 hour at room temperature and then 0.3 ml rabbit C was added to the mixture. The mixture was incubated for another hour in a 37° C. shaking water bath, washed, and residual cells cultured overnight at 37° C. After lysis of cells with anti-T4 and C, >90% of the residual cells were T8+ cells and <5% were T4+ cells. After lysis with anti-T8 and C, >90% of the remaining cells were T4+ cells and <5% were T8+ cells. These two populations will be referred to herein as the T8+ and T4+ sets, respectively.

ANALYSIS AND SEPARATION OF LYMPHOCYTE POPULATIONS WITH A FLUORESCENCE-ACTIVATED CELL SORTER

Cytofluorographic analysis of cell populations was performed by means of indirect immunofluorescence with fluorescein-conjugated (F(ab')$_2$ goat anti-mouse (Fab')$_2$ on an Epics V cell sorter (Coulter Electronics). Background fluorescence reactivity was determined with a control ascites obtained from mice immunized with nonsecreting hybridoma clons. For analysis, all monoclonal antibodies were utilized in antibody excess at dilutions of 1/250 to 1/1000.

To separate T4+ T cells into 4B4+ and 4B4−, $80 \times 10^6$ T4+ cells, which had been cultured overnight were labeled with 4 ml of a 1/250 dilution of anti-4B4 and developed with fluorescein-conjugated F(ab')$_2$ goat anti-mouse F(ab')$_2$. By using an Epics V cell sorter, the T4+ cells were separated into 4B4+ and 4B4− subpopulations.

This procedure produced two subsets of T4+ cells, a subset exhibiting high reactivity with anti-4B4 (designated "4B4+"), and a subset exhibiting low reactivity with anti-4B4 ("4B4−").

Post-sort viability was greater than 95% by trypan blue exclusion in all instances. Purity of separated T cell subsets was in excess of 95%.

CHARACTERIZATION OF ANTI-4B4

Figure 2A:
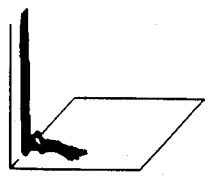
FIG. 2 is a set of graphs showing reactivities of an antibody of the invention with human T cells.
Figure 2B:
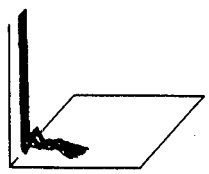
Figure 2C:
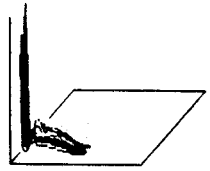

FIG. 2 is a cytofluorographic analysis of unfractionated T, T4+, and T8+ cells with anti-4B4 monoclonal antibody, displayed in logarithmic scale. As shown in FIG. 2, anti-4B4 was found to be reactive with 41±2% (mean±SE, n=13) of peripheral blood human T lymphocytes and reactive with 41±3% (mean±SE, n=14) of T4+ T lymphocytes and 43±4% (mean±SE, n=10) of T8+ T lymphocytes. Thus, 4B4+ T cells were found in both T4+ and T8+ subpopulations.

The reactivity of anti-4B4 antibody with other human lymphoid cells and cell lines is shown in Table 2, below. Anti-4B4 was found to be reactive with over 30% of both peripheral blood null cells, macrophages and thymic lymphocytes, only slightly reactive with peripheral blood B cells. Anti-4B4 was reactive with all 4 human T cell lines tested. The data in Table 2 also indicate reactivity of anti-4B4 with four lymphoblastoid B cell lines and two Burkitt's lymphoma lines. In addition, three hematopoietic cell lines tested, K562, U-937 and KG-1, were anti-4B4 reactive. These results suggest that the reactivity of anti-4B4 is not restricted to cultured cell lines of the T lineage; rather, non-T cells are also anti-4B4 reactive.

TABLE 2

Reactivity of Anti-4B4 Antibody with Human Lymphoid and Cell Lines[a]

| | |
|---|---|
| I. Lymphoids cells | |
|   B cells | ± |
|   Null cells | + |
|   MØ | + |
| II. Thymocytes | + |
| III. T cell lines | |
|   HSB | + |
|   CEM | + |
|   JM | + |
|   Molt 4 | + |
| IV. B cell | |
|   Laz 461 | + |
|   Laz 509 | + |
|   Laz 388 | + |
|   Laz 156 | + |
|   Raj | + |
|   Daudi | + |
| V. Hematopoietic lines | |
|   U-937 | + |
|   K562 | + |
|   KG-1 | + |

[a]Reactivity of anti-4B4 antibody was determined by indirect immunofluorescence on cytofluorograph (−) indicates 5% reactivity above background control; (±) indicate 5 to 30% reactivity; (+) indicate 30% reactivity.

PROLIFERATIVE RESPONSE OF UNFRACTIONATED T4+, T4+4B4+ AND T4+4B4− LYMPHOCYTES

The following procedure was carried out to determine whether proliferative activity was restricted to one or another subpopulation of T4 cells, e.g., the 4B4+ or 4B4− subset of T4+ cells.

T cells were cultured in RPMI 1640 medium with 10% human AB serum, 200 mM L-glutamine, 25 mM HEPES buffer (Microbiological Associates), 0.5% sodium bicarbonate and 1% penicillin-streptomycin. $10^5$ cells per microculture well were tested for proliferative response to an optimal dose of phytohemagglutinin (PHA) (Burroughs-Wellcome Co., Research Triangle Park, NC) and concanavalin A (Con A) (Calbiochem, San Diego, CA). The alloantigen-driven proliferative response was measured concurrently by stimulating with mitomycin C-treated Laz 156, an Epstein-Barr virus-transformed human B lymphoid line. Proliferation to tetanus toxoid (TT) (Massachusetts Department of Public Health Biological Laboratories, Jamaica Plain, MA) and mumps antigen (Microbiological Associates) were tested using 10 ug/ml final concentration and a 1:20 dilution, respectively. Macrophages were added to all lymphocyte populations at a 5% final concentration at the initiation of in vitro cultures. Mitogen-stimulated cultures were pulsed after 4 days with 0.15 uCi of tritiated thymidine ($^3$H-TdR) (1.9 Ci/mM sp. act) (Schwarz-Mann, Orangeburg, NY) per cell well; after a 16 hour incubation, the cells were harvested with a Mash II apparatus (Microbiological Associates) and $^3$H-TdR incorporation was measured on a Packard Scintillation Counter (Packard Instrument Co., Downers Grove, IL). Background $^3$H-TdR incorporation was obtained by substituting medium for mitogen. Soluble and cell surface alloantigen-driven cultures were pulsed after 5 days with $^3$H-TdR for 16 hours, harvested, and counted as above.

As shown in Table 3, differences in response to Con A, soluble antigens and autologous antigens were seen in T4+4B4+ and T4+4B4− cell populations. In response to Con A and autologous cell antigens (AMLR), T4+4B4− cells incorporated significantly more $^3$H-TdR than did the T4+4B4+ population. In contrast, in response to soluble antigens such as TT and mumps, T4+4B4+ cells incorporated significantly more $^3$H-TdR than did the T4+4B4− cell population. These differences between the proliferative response of T4+4B4+ and T4+4B4− populations were significant (P 0.05). They showed that the major proliferative activity in response to soluble antigens is found in T4+4B4+ cell population and the major proliferative activity in response to Con A and autologous cell antigen is found in the T4+4B4− cell population.

tion at the initiation of in vitro cultures. On day 7, cultures were terminated, supernatants were harvested, and IgG secretion into the supernatant was determined by solid phase radioimmunoassay (RIA) utilizing a monoclonal antibody directed at the Fc portion of the human gamma heavy chain (anti-Fc) (gifted by Dr. V. Raso, Dana-Farber Cancer Institute).

Figure 3:
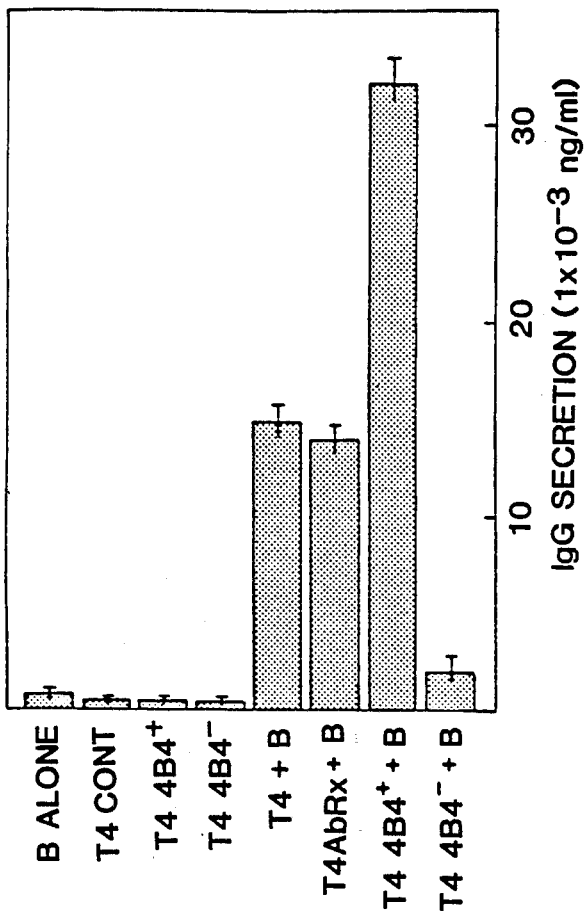
FIG. 3 is a histogram showing induction of help by various cells and cell combinations.

As shown in FIG. 3, neither B cells, unfractionated T4+ T cells, or sorted T4+ subsets secreted IgG when cultured alone. In contrast, when unfractionated T4+ T cells and B cells were mixed together and incubated with PWM, 18400±810 ng of IgG were secreted per milliliter of culture supernatant. Incubation of T4+ T cells with anti-4B4 had no effect on the help these cells provided to B cells.

When equal numbers of T4+4B4+ and T4+4B4− cells were added to separate cultures of autologous B cells, the IgG secretion induced by the T4+4B4+ T cell subset was approximately 15 times greater than that

| Proliferative Responses of Unfractionated T4+ T Cells and T4+4B4+ and T4+4B4− Subpopulations to Nonspecific Mitogens or Antigenic Stimulation | | | | |
|---|---|---|---|---|
| Proliferative Response | T4+ T Cells | T4+ T Cells Treated with Anti-4B4 an G/M FITC | T4+4B4+ T Cells | T4+4B4− T Cells |
| Exp 1 | | | | |
| Media | 875 ± 217[a] | 497 ± 194 | 505 ± 196 | 211 ± 108 |
| PHA (0.25 ug/ml) | 35847 ± 1018 | 32338 ± 624 | 25955 ± 2054 | 46586 ± 3175 |
| Con A (30 ug/ml) | 55127 ± 1296 | 52609 ± 3483 | 17222 ± 496 | 47444 ± 2592 |
| Con A (60 ug/ml) | 57626 ± 1632 | 51782 ± 1135 | 24039 ± 1198 | 63160 ± 1384 |
| Tetanus Toxoid | 28095 ± 5192 | 44312 ± 4349 | 106027 ± 1191 | 5387 ± 2170 |
| Mumps | 18853 ± 2008 | 24822 ± 1955 | 59405 ± 4355 | 10342 ± 595 |
| Allo E− | 25657 ± 2497 | 23421 ± 3980 | 25003 ± 2149 | 19614 ± 2563 |
| Auto E− | 5120 ± 2117 | 5321 ± 1962 | 705 ± 142 | 11753 ± 1399 |
| Exp 2 | | | | |
| Media | 643 ± 194 | 816 ± 254 | 542 ± 172 | 426 ± 102 |
| PHA (0.25 ug/ml) | 73512 ± 2459 | 61493 ± 3328 | 47210 ± 3895 | 70873 ± 4944 |
| Con A (30 ug/ml) | 65657 ± 4443 | 67193 ± 2492 | 16849 ± 1492 | 67548 ± 3129 |
| Con A (60 ug/ml) | 83238 ± 3440 | 76692 ± 4621 | 31246 ± 2456 | 105853 ± 5644 |
| Tetanus Toxoid | 21649 ± 1493 | 21864 ± 2279 | 80822 ± 6419 | 1054 ± 252 |
| Mumps | 7687 ± 1944 | 6721 ± 1452 | 8964 ± 1358 | 1631 ± 24 |
| Allo E− | 33164 ± 1258 | 42964 ± 3654 | 31860 ± 1459 | 291110 ± 18 |
| Auto E− | 4050 ± 329 | 4557 ± 218 | 2255 ± 872 | 8916 ± 47 |

[a]Values are expressed as the mean ± SEM of triplicate samples.

PWM-STIMULATED IgG SYNTHESIS BY B CELLS CO-CULTURED WITH T4+4B4+ AND T4+4B4− LYMPHOCYTES

In order to determine whether T cell help for B cell immunoglobulin production was restricted to the T4+4B4+ or T4+4B4− T cell subset, unfractionated T4+ T cells or T4+4B4+ and T4+4B4− cells were mixed with autologous B lymphocytes, stimulated with PWM in vitro, and total IgG production was measured after 7 days in culture.

Unfractionated and separated populations of lymphocytes were cultured in round-bottomed microtiter culture plates (Falcon) at 37° C. in a humidified atmosphere with 5% $CO_2$ for 7 days in RPMI 1640 supplemented with 20% heat-inactivated fetal calf serum (Microbiological Associates), 0.5% sodium bicarbonate, 200 mM L-glutamine, 25 mM HEPES and 1% penicillin-streptomycin. To determine the effect of various subsets of the T4 cells on secretion of IgG by autologous plasma cells, various numbers of unfractionated T4+ T cells or purified T4+4B4+ and T4+4B4− T cell subsets were added to $5 \times 10^4$ B cells in a volume of 1 ml. To this was added 0.1 ml of pokeweed mitogen (PWM) (Gibco Laboratories, Grand Island Biological Co., Grand Island, NY) at a 1:50 dilution. Macrophages were added to all populations at a 5% final concentraobtained with the combination of T4+4B4− and B cells (33000±2100 ng vs. 1700±100 ng). Furthermore, a quantitative comparison of the helper function provided by T4+4B4+ and T4+4B4− T cells for B cell IgG production (Table 4, below) showed that the helper effect of T4+4B4+ T cells was strikingly greater than that of T4+4B4− T cells at any number of T cells and B cells tested. Thus, the majority of helper activity for the antibody production in response to PWM by B cells was found within the T4+4B4+ subset of cells, and the T4+4B4− had minimal helper effect in this interaction.

TABLE 4

| Quantitative Comparison of Helper Function Provided by T4+4B4+ and T4+4B4− T Cells for B cell IgG Production | | | | |
|---|---|---|---|---|
| | IgG (ng/ml) | | | |
| Lymphoid Population | Exp 1 | Exp 2 | Exp 3 | Exp 4 |
| B ($5 \times 10^4$)[a] | 250[b] | 600 | 420 | 320 |
| B ($5 \times 10^4$) + T4+4B4+ ($5 \times 10^3$) | 6000 | 3400 | 2400 | 17200 |
| + T4+4B4+ ($1 \times 10^4$) | 5600 | 4800 | 3800 | 20000 |
| + T4+4B4+ ($2 \times 10^4$) | 16000 | 14800 | 5200 | 32000 |
| + T4+4B4+ ($4 \times 10^4$) | 16200 | 15200 | 10000 | 32400 |
| 5 ($5 \times 10^4$) + T4+4B4− ($5 \times 10^3$) | 2480 | 1680 | 480 | 2400 |
| + T4+4B4− ($1 \times 10^4$) | 2800 | 2400 | 1160 | 2600 |
| + T4+4B4− ($3 \times 10^4$) | 960 | 2800 | 1120 | 2900 |
| + T4+4B4− ($5 \times 10^4$) | 300 | 2200 | 1160 | 1800 |

TABLE 4-continued

Quantitative Comparison of Helper Function Provided by
T4+4B4+ and T4+4B4− T Cells for B cell IgG Production

| Lymphoid Population | IgG (ng/ml) | | | |
|---|---|---|---|---|
| | Exp 1 | Exp 2 | Exp 3 | Exp 4 |
| T4+4B4+ | 300 | 150 | 200 | 150 |
| T4+4B4− | 180 | 200 | 150 | 250 |

[a]Figures in parentheses represent the number of lymphocytes of each population added to the culture.
[b]Values are expressed as mean ng/ml of triplicate samples. SE was always less than 10%.

EFFECT OF T4+4B4+ OR T4+4B4− CELLS ON THE GENERATION OF SUPPRESSOR EFFECTOR CELLS

The following procedure was carried out to determine whether these T4+4B4+ and T4+4B4− subsets of cells had any effect on the generation of suppressor function.

Varying numbers of T4+4B4+ or T4+4B4− cells were added to a constant number of B cells ($5 \times 10^4$) in the presence of PWM. Fractionated T4+4B4+ or T4+4B4− cells ($2 \times 10^4$) were added to these cells. As shown in Table 5 (part A and B), when increasing numbers of T8+ cells were added to T4+4B4− cells and B cells, marked suppression in the IgG production was observed. In contrast, when moderate or low numbers of T8+ cells were added to T4+4B4+ cells and B cells, no or only a slight diminution in IgG production was seen. It should be noted that when excess numbers of T8+ cells ($4 \times 10^4$) were added to T4+4B4+ cells and B cells, a moderate amount of suppression in IgG production was seen. These results indicate that T4+4B4− cells are very efficient in the generation of suppression of IgG production by B cells in the presence of T8+ cells.

To demonstrate directly that T4+4B4− cells are necessary for the induction of suppression, varying numbers of T4+4B4+ or T4+4B4− cells were added to a constant number of B cells ($5 \times 10^4$) and T4+2H4− or T4+2H4+ cells ($2 \times 10^4$) and T8+ cells ($1 \times 10^4$) in the presence of PWM. As shown in Table 5 (part C and D), when increasing numbers of T4+4B4− cells were added to a constant number of B cells, T4+4B4+ cells and T8 cells, increasing suppression of IgG production was observed (10000 ng vs 680 ng, 6800 ng vs 3200 ng, 6000 mg vs 810 ng). In contrast, the addition of increasing numbers of T4+4B4+ cells resulted in enhanced IgG production. These results suggest that T4+4B4− cells activate or induce T8+ cells to become suppressor effector cells.

TABLE 5

Effect of T4+4B4+ or T4+4B4− Subsets on the Generation of Suppressor Effector Cells

| Cell Combination[a] | Cells Added | Exp 1 | Exp 2 | Exp 3 |
|---|---|---|---|---|
| | T8 Cells Added | | | |
| A. B + T4+4B4+ | 0 | 16000[b] | 14000 | 8000 |
| | $5 \times 10^3$ | 14000 (12)[c] | 16000 (0) | 7600 (5) |
| | $1 \times 10^4$ | 10400 (35) | 16800 (0) | 6400 (20) |
| | $2 \times 10^4$ | 11000 (31) | 12400 (11) | 6200 (23) |
| | $4 \times 10^4$ | 5000 (69) | 5600 (60) | 1900 (76) |
| B. B + T4+4B4− | 0 | 2520 | 3600 | 3000 |
| | $5 \times 10^3$ | 720 (71) | 2800 (23) | 2080 (31) |
| | $1 \times 10^4$ | 560 (78) | 1600 (56) | 720 (76) |
| | $2 \times 10^4$ | 80 (97) | 1000 (72) | 640 (79) |
| | $4 \times 10^4$ | 80 (99) | 370 (90) | 80 (97) |
| | T4+ 4B4− added | | | |
| C. B + T4+4B4+ + T8 | 0 | 10000 | 16800 | 6000 |
| | $1 + 10^4$ | 4400 (56) | 7200 (57) | 3000 (50) |
| | $2 \times 10^4$ | 1400 (86) | — | 2720 (55) |
| | $4 \times 10^4$ | 680 (93) | 3200 (81) | 810 (87) |
| | T4+4B4+ added | | | |
| D. B + T4+4B4− + T8 | 0 | 120 | 1600 | 1120 |
| | $1 \times 10^4$ | 180 (0) | 7600 (0) | 2000 (0) |
| | $2 \times 10^4$ | 1020 (0) | — | 3400 (0) |
| | $4 \times 10^4$ | 2800 (0) | 16400 (0) | 7200 (0) |

[a]Varying numbers of T8+ cells (group A, B) or varying numbers of T4+4B4+ or T4+4B4− (group C, D) were added to a constant number of B cells ($5 \times 10^4$) and T4+4B4+ ($2 \times 10^4$) or T4+4B4− ($2 \times 10^4$) cells in the presence of PWM without (group A, B) and with $1 \times 10^4$ T8+ cells (group C, D).
[b]Values are expressed as mean ng/ml of triplicate samples. SEM was less than 10%.
[c]Number in parentheses equal % suppression calculated as the following formula:

$$\frac{\text{Control IgG} - \text{IgG observed by the addition of T8+ cells or T4+4B4+ or T4+4B4− cells}}{\text{Control IgG Production}} \times 100$$

THE RELATIONSHIP BETWEEN THE T4+2H4+ AND T4+4B4+ CELL SUBSETS

T4+2H4+ lymphocytes proliferate well to Con A stimulation, but poorly to soluble antigen stimulation and provide poor help to B cells for PWM-induced Ig synthesis; T4+2H4− cells proliferate poorly upon stimulation with Con A but well on exposure to soluble antigen and provide a good helper signal for PWM-induced Ig synthesis. Moreover, this antibody defines the subset of T4+ cells which is the inducer of the T8+ suppressor cells. In contrast, T4+4B4+ lymphocytes proliferate poorly upon stimulation with Con A but well on exposure to soluble antigen and provide a good helper signal for PWM-induced Ig synthesis. T4+4B4− cells proliferate well to Con A stimulation and provide poor help to B cells for PWM-induced Ig synthesis. Furthermore, the T4+4B4− lymphocyte population contains the suppressor inducer activity. Thus, functionally, the anti-4B4 antibody reacts the T cell subset which is the reciprocal of that defined by anti-2H4.

Figure 4B:
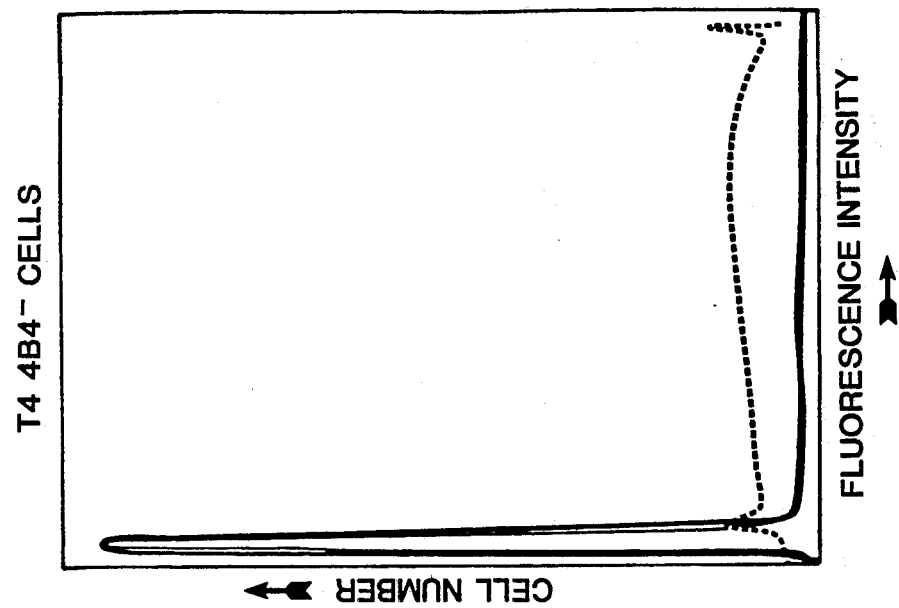
FIG. 4 is a pair of graphs showing the relationship between cells carrying the antigenic determinant of the invention and another antigen.
Figure 4A:
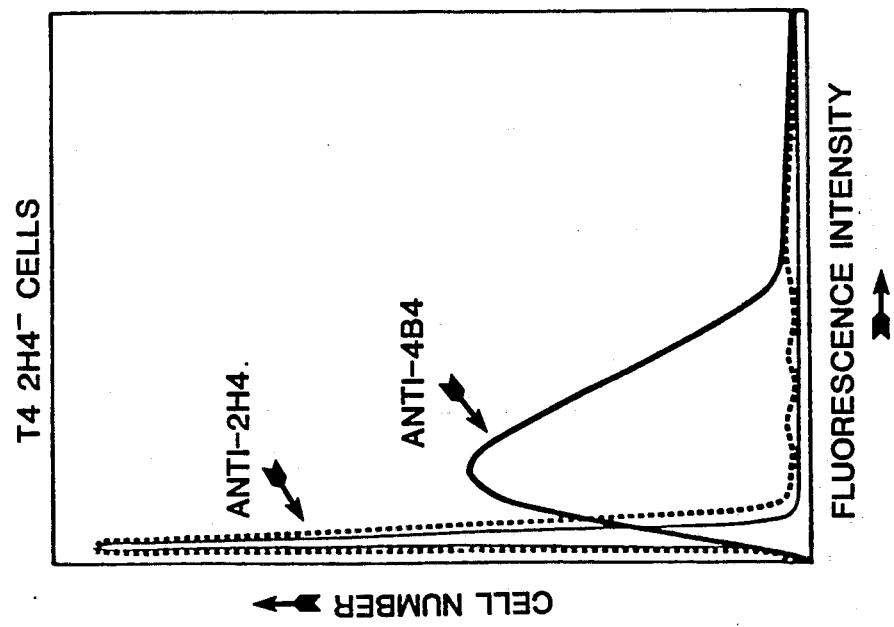

As shown in FIG. 4, anti-4B4 reacts wtih almost all T4+2H4− cells, and anti-2H4 reacts with almost all T4+4B4− cells. Furthermore, using a double fluorescence staining technique with a 4B4-FITC conjugate and 2H4-phycoerythrin conjugate, it was found that 4B4+2H4+ cells constitute less than 10% of the total T4+ population of cells. Thus, functionally and phenotypically the T4+ cell subset defined by anti-4B4 is reciprocal to that subset defined by anti-2H4.

CHARACTERIZATION OF THE ANTIGEN DETECTED BY ANTI-4B4

The following procedures were carried out to label and characterize the cell surface antigen detected by anti-4B4.

Splenic T cells were prepared by E-rosetting followed by lysis with anti-B1 antibody, anti-Mo1 antibody and complement. After removal of dead cells or Ficoll-Hypaque gradients, the cells were labelled by a modification of the Lactoperoxidase technique. Labelled cells were lysed for 45 min in 0.5% Triton X-100 in 0.05M Tris HCl/0.4M Nacl/2 mM PMSF/2 mM EDTA/50 mM iodoacetamide. Cell nuclei and other insoluble material was removed by centrifugation at 1000 g for 10 min.

Immunoprecipitation cell lysates was performed by centrifuging at 100,000 g for 10 minutes and the supernatant pre-cleared twice with Pansorbin (Calbiochem, La Jolla, CA). The supernatant was then cleared with an irrelevant antibody coupled to Sepharose 4B. The pre-cleared supernatant was mixed with 4B4-Sepharose 4B conjugates and incubated for 4 hours at 4° C. After this, the beads were washed 4 times with cell lysis buffer. Complexes were eluted from the beads by boiling in SDS sample buffer and analyzed by 10% SDS polyacrylamide gel electrophoresis (SDS-PAGE).

Figure 5:
FIG. 5 is an autoradiograph biochemically characterizing the antigenic determinant of the invention.

As shown in FIG. 5, lane 2, when run under non-reducing conditions, the 4B4 antigen consists of two bands between 125–135 KD. By contrast, under reducing conditions the antigen (lane 4) runs as a single broad band of 130–140 KD. The apparent two band structure and slightly faster mobility under non-reducing conditions reflect the effects of glycosylation differences and interchain disulfide bonding.

DEPOSIT

An essentially pure culture of hybridoma cells producing anti-4B4 antibody has been deposited in the American Type Culture Collection, Rockville, Md., and given ATCC Accession No. HB 8703 dated Jan. 22, 1985.

USE

The monoclonal antibody of the invention can be labeled with a detectable lable, e.g., a radiolabel by conventional procedures, and provide a quantitative measurement of 4H4+ cells in biological samples or in vivo.

Because of its specificity for 4H4+ T-cells, the monoclonal antibody of the invention can be used to detect the presence of these cell types in biological samples. The monoclonal antibody of the invention can be used as a diagnostic aid in characterizing the cell types involved in JRA, SLE, Sjogren's disease and other autoimmune disorders in which T-cells are implicated, and of various lymphomas and leukemias arising from T-cells. In addition, in vivo imaging using radiolabeled monoclonal antibody of the invention can provide a noninvasive means for detecting and localizing these cell types, e.g., tumors of T-cell origin.

The 4B4 antibody detects a major subpopulation of T4 cells with immunoregulatory activity. The ability to detect this inducer of help in the T4 population may be important for both diagnosis and treatment of various immunoregulatory disorders. The removal of the inducer of help may be a major aid in the transplantation of a variety of tissues including kidney heart, bone marrow as examples. The residual inducers of suppression, i.e. the 4B4 negative population may allow for the establishment of grafts. Moreover, the therapeutic administration of this antibody either alone or coupled to a radioisotope, drug or toxin may have therapeutic benefit in autoimmune diseases or in patients receiving organ transplants since the mechanism whereby transplants are rejected involves the activation of the immune response.

Other embodiments are within the following claims. What is claimed is:

1. Hybridoma cells identical to those of the cell line identified as ATCC Deposit No. HB 8703.

2. A monoclonal antibody which binds specifically to a non-human primate cell, said monoclonal antibody being further characterized in that it binds specifically with a specific antigenic determinant on a first subset of human T4+ cells, which cells are capable of inducing, in the presence of pokeweed mitogen, a degree of IgG secretion in human B cells, it does not bind specifically with a second subset of human T4+ cells, which cells are capable of inducing, in the presence of pokeweed mitogen, a lower degree of IgG secretion in human B cells, said degree of IgG secretion of said first subset being approximately 15 times greater than that of said second subset, it is of the IgG1 isotype, and it is produced by murine hybridoma cell line identified as ATCC HB 8703.

3. A monoclonal antibody as claimed in claim 2 in which said antigenic determinant has a molecular weight of approximately 130,000–140,000 daltons under reducing conditions, and two molecular weights between approximately 125,000 and 135,000 daltons under non-reducing conditions.

4. A monoclonal antibody as claimed in claim 2 in which said specific binding and lack of binding are determined by indirect immunofluorescence.

5. A method of distinguishing a first subset of human T4+ cells from a second subset of human T4+ cells, said method comprising contacting a set of said T4+ cells containing both said subsets with a monoclonal antibody produced by the hybrid cell line having the identifying characteristics of ATCC HB 8703 to permit said monoclonal antibody to selectively bind specifically to both said subsets of T4+ cells and subjecting said set of T4+ cells to sorting based on indirect immunofluorescence.

6. A method as claimed in claim 5 in which said first subset is of T4+ cells which are capable of inducing, in the presence of pokeweed mitogen, a degree of IgG secretion in human B cells and said second subset is of T4+ cells which are capable of inducing, in the presence of pokeweed mitogen, a lower degree of IgG secretion in human B cells, said degree of IgG secretion of said first subset being approximately 15 times greater than that of said second subset.

* * * * *